(12) United States Patent
Warren (10) Patent No.: US 10,070,877 B2
(45) Date of Patent: Sep. 11, 2018

(54) REENTRY DEVICE (71) Applicant: Cook Medical Technologies LLC, Bloomington, IN (US)

(72) Inventor: Shavonna Warren, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 239 days.

(21) Appl. No.: 15/046,956

(22) Filed: Mar. 14, 2016

(65) Prior Publication Data

US 2016/0192952 A1 Jul. 7, 2016

Related U.S. Application Data

(62) Division of application No. 13/608,418, filed on Sep. 10, 2012.

(51) Int. Cl.
| | |
|---|---|
| *A61F 11/00* | (2006.01) |
| *A61B 17/22* | (2006.01) |
| *A61M 25/10* | (2013.01) |
| *A61M 25/01* | (2006.01) |
| *A61B 17/00* | (2006.01) |

(52) U.S. Cl.
CPC .......... *A61B 17/22* (2013.01); *A61M 25/0108* (2013.01); *A61M 25/104* (2013.01); *A61B 2017/00243* (2013.01); *A61B 2017/00778* (2013.01); *A61B 2017/22072* (2013.01); *A61B 2017/22074* (2013.01); *A61B 2017/22094* (2013.01); *A61B 2017/22095* (2013.01); *A61M 25/0194* (2013.01); *A61M 2025/018* (2013.01); *A61M 2025/0197* (2013.01)

(58) Field of Classification Search
CPC .......... A61B 17/22; A61B 2017/22072; A61B 2017/22074; A61B 2017/22094; A61B 2017/22095; A61M 25/0194; A61M 2025/0197
See application file for complete search history.

(56) References Cited

U.S. PATENT DOCUMENTS

| | | |
|---|---|---|
| 5,387,087 A | 2/1995 | Chen |
| 2006/0276749 A1* | 12/2006 | Selmon ..................... A61B 6/12 604/164.01 |
| 2008/0125748 A1* | 5/2008 | Patel ................. A61M 25/0084 604/509 |

(Continued)

*Primary Examiner* — Robert Lynch
(74) *Attorney, Agent, or Firm* — Brinks Gilson & Lione (57) ABSTRACT

The disclosure provides apparatus and methods for reentering a true lumen. The reentry catheter includes a shaft that includes a proximal opening in a proximal end of the shaft, a J-shaped filler in a distal end of the shaft, and a distal side opening in a sidewall of the shaft. The distal side opening is adjacent to the J-shaped filler. A passageway extends between the proximal opening and the distal side opening. The proximal opening, the distal side opening, and the passageway each are configured for the passage of an elongate medical device there through. A movable cover is hingedly attached to the sidewall of the shaft biased in a closed position and configured to occlude the distal side opening when in the closed position. The elongate medical device is configured to open the movable cover, the movable cover is configured to facilitate reentry to a true lumen.

15 Claims, 8 Drawing Sheets

(56) References Cited

U.S. PATENT DOCUMENTS

2010/0286627 A1* 11/2010 Hardin .................. A61B 90/39
604/264
2014/0018837 A1* 1/2014 Zhou ..................... A61M 25/09
606/194
2014/0371718 A1* 12/2014 Alvarez ............ A61M 25/0074
604/510

* cited by examiner

REENTRY DEVICE

This application is a divisional of U.S. application Ser. No. 13/608,418, filed Sep. 10, 2012, which is titled "REENTRY DEVICE", the contents of which is incorporated herein by reference.

BACKGROUND

The present disclosure relates generally to apparatus and methods for catheters, and more specifically, for a reentry catheter device.

Chronic total occlusions (CTOs) are a common finding in patients with coronary artery disease. Treatment of coronary CTOs remains a challenging obstacle, posing a considerable barrier to achieving successful complete revascularization. The choice of revascularization includes endovascular treatment, which is a very complicated and expensive surgery.

Endovascular treatment of CTOs is increasing while the recanalization through CTO remains challenging. The most common method for crossing occlusions uses hydrophilic wires and catheters in the subintimal plane for a portion of the occlusion. One of the primary limitations to successful treatment of CTOs is reported to be the failure to re-enter the true lumen after subintimal crossing of the occlusion.

An additional limitation in some cases is that the true lumen reentry is not achieved until subintimal passage to a site significantly remote from the level of vessel lumen patency, which causes subintimal angioplasty or stenting to extend beyond the occluded segment. Further, a reentry device may cause unnecessary trauma during the reentry procedure. Therefore, it would be desirable to provide an inexpensive apparatus and a relatively simple method for re-entering the true lumen at the desired region close to the occlusion without unnecessary trauma.

SUMMARY

The present disclosure provides apparatus and methods for removing thrombus outside of a reentry catheter by providing a third lumen with an operable member in the reentry catheter.

One embodiment of the reentry catheter comprises a shaft that includes a proximal opening in a proximal end of the shaft, a J-shaped filler in a distal end of the shaft, and a distal side opening in a sidewall of the shaft. The distal side opening is adjacent to the J-shaped filler. A passageway extends between the proximal opening and the distal side opening. The proximal opening, the distal side opening, and the passageway each are configured for the passage of an elongate medical device there through. A movable cover is hingedly attached to the sidewall of the shaft. The movable cover is biased in a closed position and configured to occlude the distal side opening when in the closed position. The elongate medical device is configured to open the movable cover, and the movable cover is configured to facilitate reentry to a true lumen.

A method to use the above embodiment of the reentry catheter during an endovascular treatment includes: inserting a wire guide by puncturing through a vessel wall of the true lumen. An operator advances a first catheter having a distal opening along a wire guide until the distal opening is distal to the occlusion. The operator then removes the wire guide from the first catheter and advances a reentry catheter inside the first catheter. The reentry catheter includes a proximal end of the shaft, a J-shaped filler in a distal end of the shaft, a distal side opening in a sidewall of the shaft, the distal side opening adjacent to the J-shaped filler, and a passageway extending between the proximal opening and the distal side opening, the proximal opening, the distal side opening, and the passageway each being configured for the passage of an elongate medical device there through, a movable cover hingedly attached to the sidewall of the shaft, which is biased in a closed position and configured to occlude the distal side opening when in the closed position. The operator advances the reentry catheter until the distal side opening is distal to the distal opening of the first catheter. The reentry catheter reenters the true lumen by opening the movable cover with the elongate medical device.

BRIEF DESCRIPTION OF THE DRAWINGS

The disclosure can be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

DETAILED DESCRIPTION OF THE PREFERRED EMBODIMENTS

In the present application, the term "proximal" refers to a direction that is generally toward a physician during a medical procedure, while the term "distal" refers to a direction that is generally toward a target site within a patient's anatomy during a medical procedure. The figures shown are for illustration purpose only and not to scale. The actual catheters comply with the standard manufacture and catheter design procedures.

Figure 1:
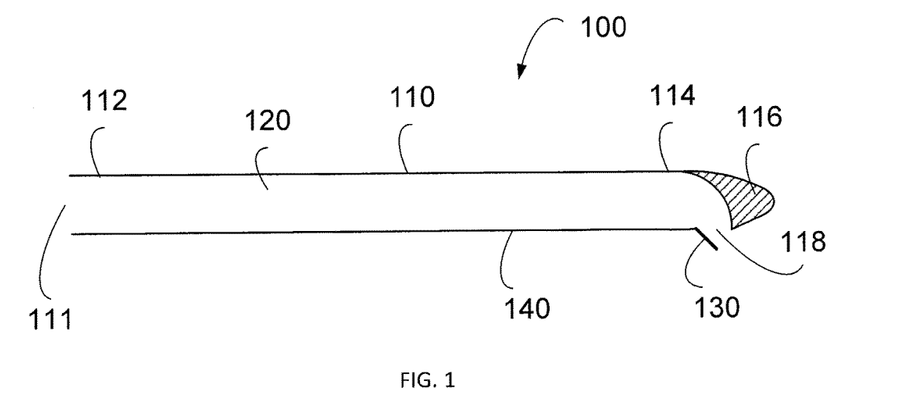
FIG. 1 is an illustration of a first embodiment of a reentry catheter with a movable cover in a closed position.
Figure 2:
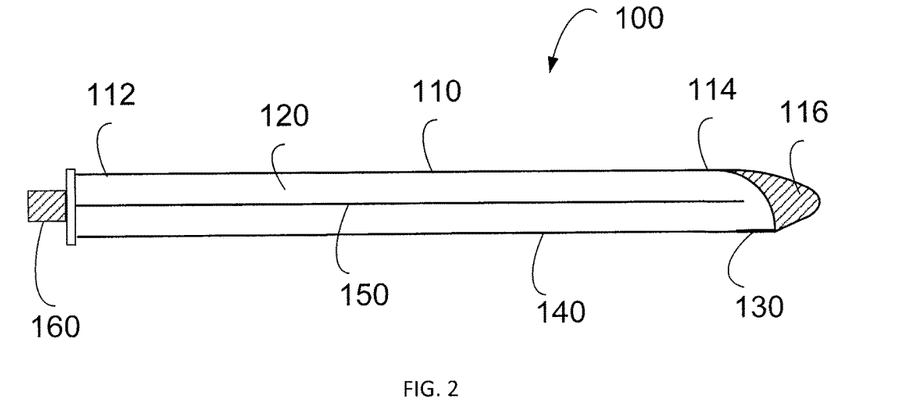
FIG. 2 is an illustration of the first embodiment of a reentry catheter with an elongate medical device.
Figure 3:
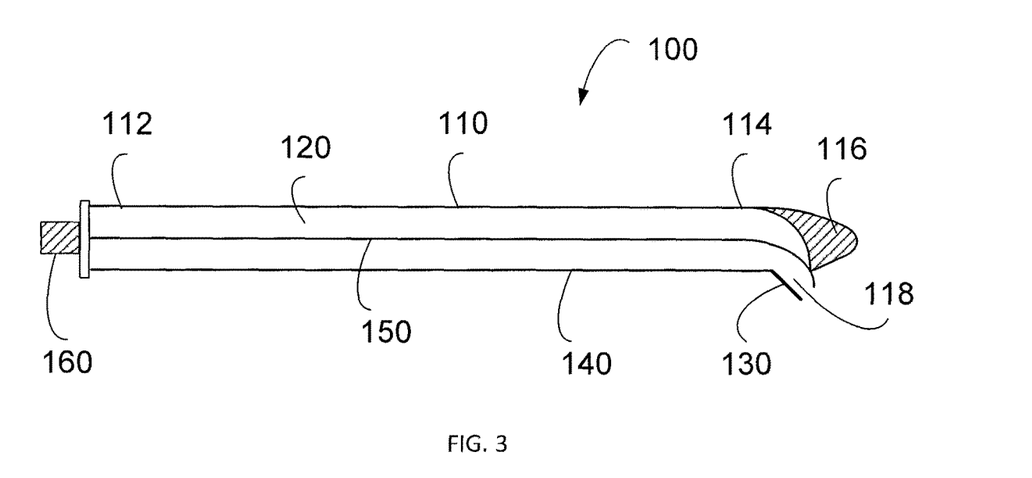
FIG. 3 is an illustration of the first embodiment of a reentry catheter with a movable cover in an open position.

Referring now to FIGS. 1-3, a first embodiment of a reentry catheter 100 for an endovascular treatment is described. The reentry catheter 100 includes an elongate shaft 110 having a proximal opening 111 in a proximal end 112 of the elongate shaft 110, a J-shaped filler 116 in a distal end 114 of the elongate shaft 110, a distal side opening 118 in a sidewall 140 of the elongate shaft 110. The distal side opening 118 is adjacent to the J-shaped filler 116. A passageway 120 extends between the proximal opening 111 and the distal side opening 118. The proximal opening 111, the distal side opening 118, and the passageway 120 are each configured for the passage of an elongate medical device 150 there through.

The elongate medical device 150 may be a wire guide or other medical device that is configured to pass through a catheter. The elongate medical device 150 may include a manipulating device 160 at the proximal end thereof. A movable cover 130 is hingedly attached to the sidewall 140 of the shaft 110. The movable cover 130 is biased in a closed position and configured to occlude the distal side opening when in the closed position as shown in FIG. 2. The biased closed movable cover 130 provides a safer reentry procedure with less risk of trauma to the vessel. The elongate medical device 150, such as a wire guide, is configured to open the movable cover 130.

FIG. 3 illustrates the first embodiment of a reentry catheter 100 with a movable cover 130 in an open position. In FIG. 3, a distal end of the elongate medical device 150 pops open the movable cover 130 and a distal end of the elongate medical device 150 exits through the distal side opening 118. An operator may gain reentry to a true lumen by advancing the elongate medical device 150 further so that the distal end of the elongate medical device 150 punctures the vessel wall. Alternatively or additionally, the opened movable cover 130 may be configured to facilitate reentry to a true lumen by supporting and guiding the distal end of the elongate medical device 150. For example, when the movable cover is in an open position, the biasing of the movable cover 130 and the J-shaped filler 116 confines the movement of the elongate device 150 and thus guides its reentry direction to the desired position within a relatively narrow angle. To help the operator identify the precise reentry location, the distal side opening 118 is marked by surrounding radiopaque material in the sidewall 140. Similarly, the J-shaped filler 116 includes radiopaque material to help the operator locate the reentry catheter in the vessel way. Additionally, the elongate medical device 150 includes radiopaque material at a distal end thereof. For example, the elongate medical device may include a radiopaque catheter balloon at the distal end.

A nitinol material may be used because of its soft property to create the proximal end 112 of the reentry catheter 100. Thus, the reentry catheter may easily be manipulated in the anatomy to accommodate the angles, curves, and turns. The diameter of the reentry catheter 100 is in the range of about 0.035 mm to about 0.038 mm to accommodate the elongate medical device 150 having a diameter of about 0.014 mm.

Figure 4:
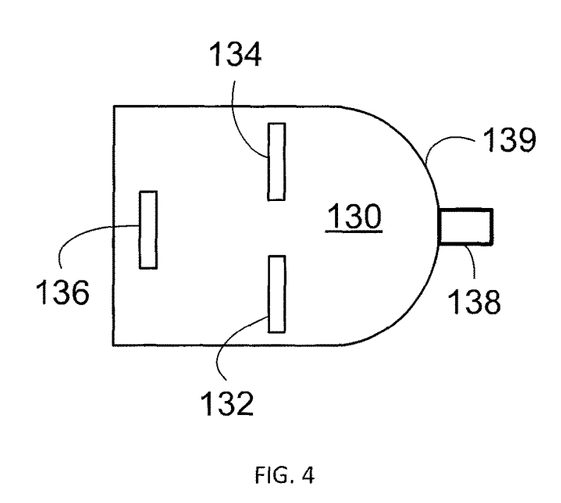
FIG. 4 is an illustration of an enlarged cross section view of an embodiment of the movable cover of a reentry catheter.

FIG. 4 illustrates an enlarged cross section view of an embodiment of the movable cover 130 of a reentry catheter. The movable cover 130 includes one of the following mechanisms: a spring, a magnet, a stopper, or a hinge pin. The movable cover 130 may also include shape memory material. The movable cover 130 includes a plurality of radiopaque markers: 132, 134, and 136. The radiopaque markers: 132, 134, and 136 may have a rectangular shape or other reasonable shapes to help the operator locate the position of the movable cover 130 accurately. The movable cover 130 may have a different shape so that it may gain access to a true lumen.

Alternatively or additionally, the movable cover 130 may include a reentry needle 138 at the distal end thereof. When the movable cover 130 includes the reentry needle 138, the side wall 140 also includes a sheathe that accommodates the needle 138. Alternatively or additionally, the movable cover 130 may, the movable cover 130 may include a relatively sharp edge 139 configured to partially penetrate the vessel wall. In one embodiment, by including the radiopaque markers and one of the relatively sharp edge and the reentry needle in the movable cover, the reentry catheter provides an accurate reentry method described below. The operator can use standard wire guide catheters to perform reentry procedures with the reentry catheter.

Figure 5:
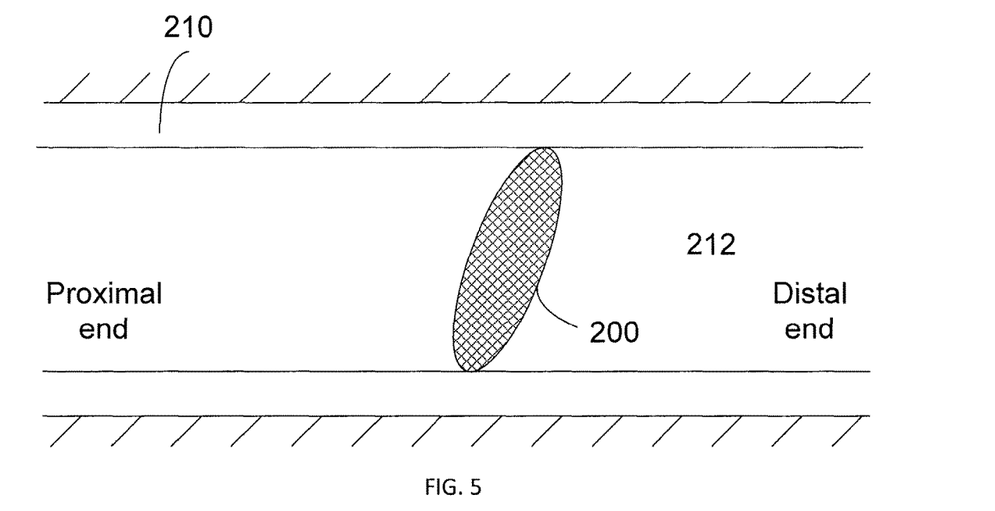
FIG. 5 illustrates a vessel having an occlusion.

FIG. 5 illustrates a vessel having an occlusion. The vessel includes a vessel way 210 and an occlusion 200 that blocks most of the blood flow in the vessel. A desired reentry location to the true lumen 212 is at a point near the distal end of the occlusion 200.

Figure 6:
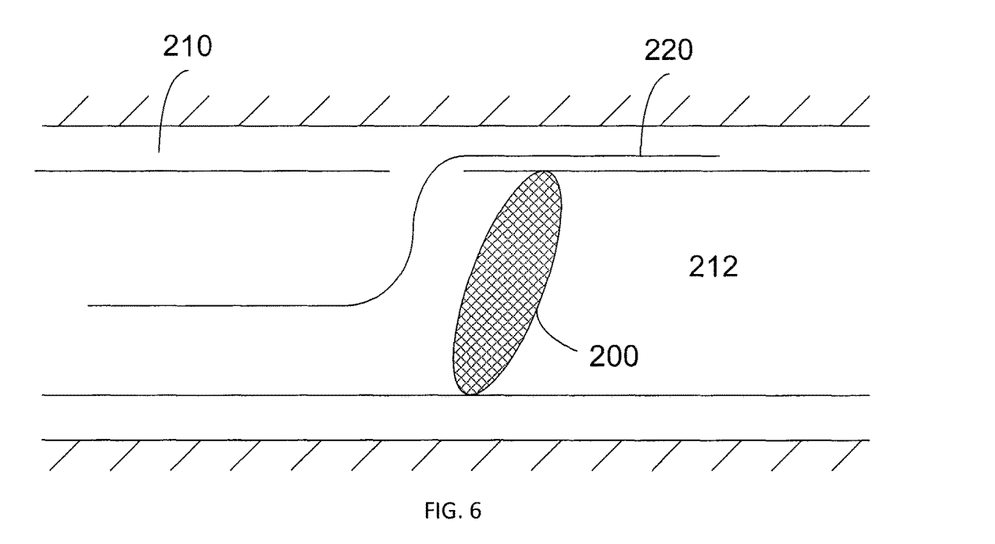
FIG. 6 illustrates a first step in the method of using a reentry catheter.

FIG. 6 illustrates a first step in the method of using a reentry catheter. In this step, an operator inserts a wire guide 220 by puncturing through a vessel wall 210 of the true lumen 212. The wire guide 220 punctures the vessel wall 210 at a location proximal to the occlusion 200.

To achieve a successful true lumen reentry, the reentry region should be distal and adjacent to the occlusion 200.

Figure 7:
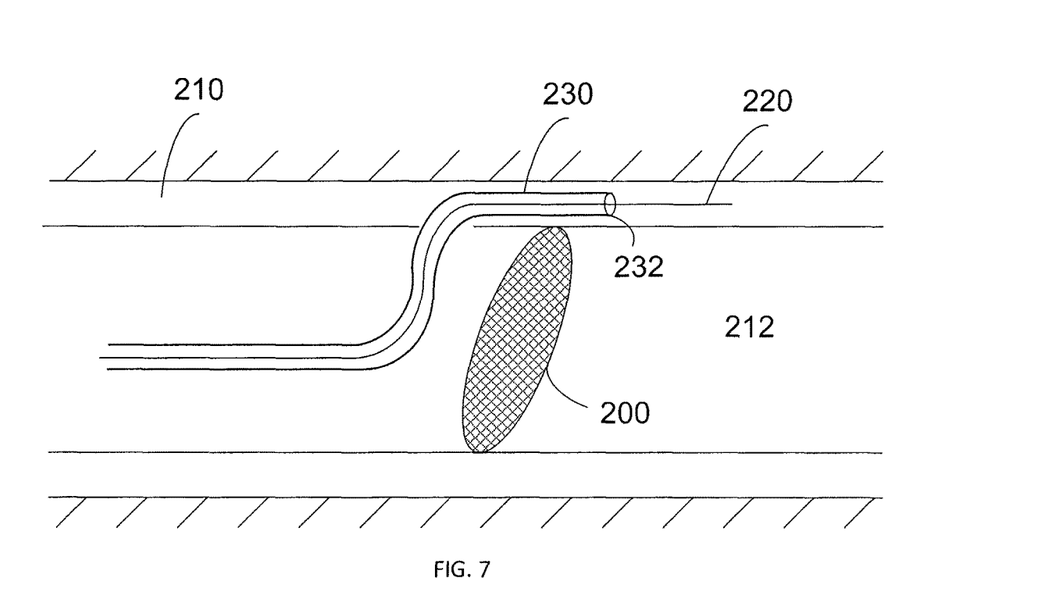
FIG. 7 illustrates a second step in the method of using a reentry catheter.

FIG. 7 illustrates a second step in the method of using a reentry catheter. In this step, the operator advances a first catheter 230 having a distal opening 232 along a wire guide until the distal opening 232 is distal to the occlusion 200. The distal opening may be marked with radiopaque material or other imaging agent to identify the position of the distal opening.

Figure 8:
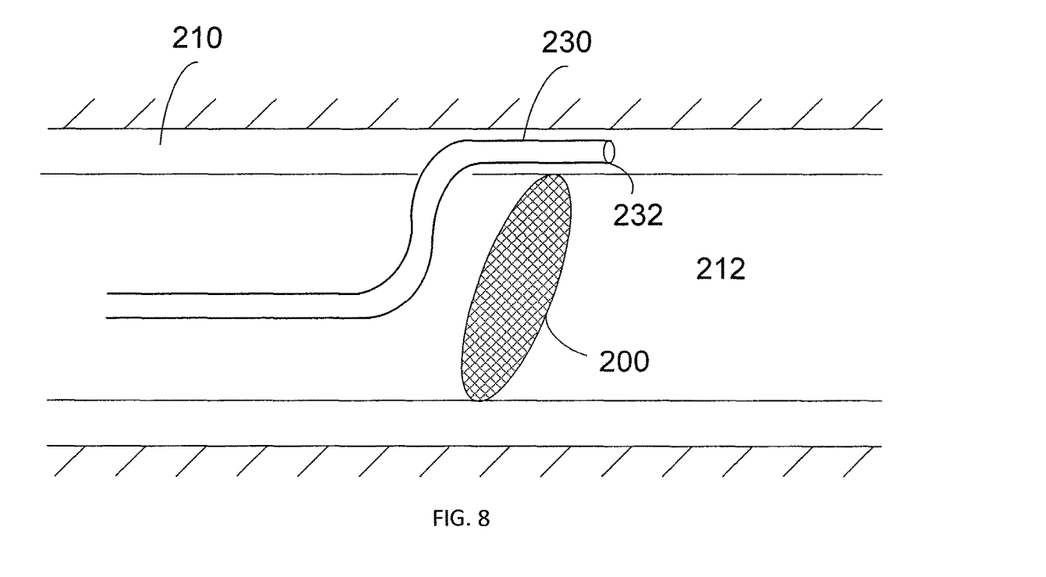
FIG. 8 illustrates a third step in the method of using a reentry catheter.

FIG. 8 illustrates a third step in the method of using a reentry catheter. In this step, the wire guide 220 is removed from the first catheter 230.

Figure 9:
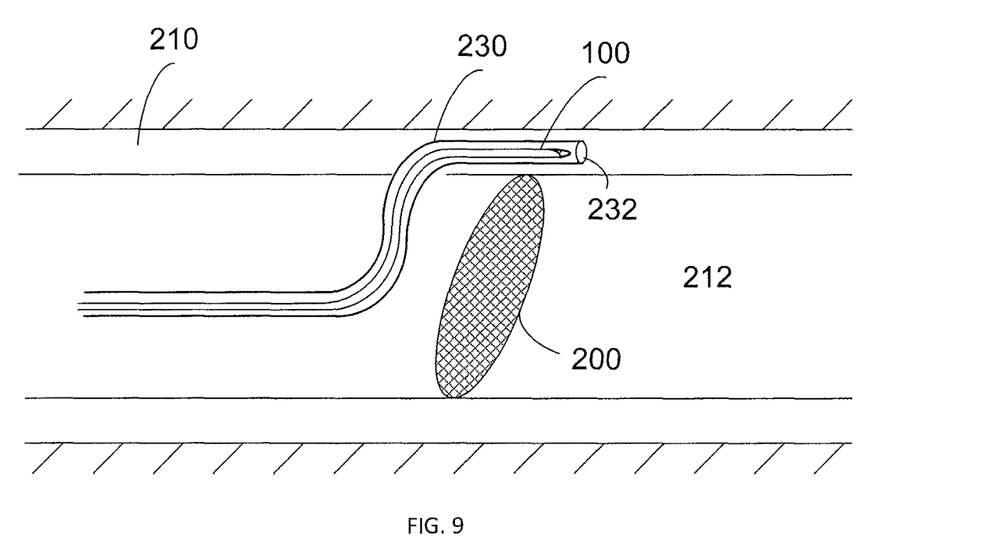
FIG. 9 illustrates a fourth step in the method of using a reentry catheter.

FIG. 9 illustrates a fourth step in the method of using a reentry catheter. In this step, the operator advances an aforementioned reentry catheter 100 inside the first catheter 230. The reentry catheter 100 includes the elongate shaft having a proximal opening in a proximal end of the elongate shaft, a J-shaped filler in a distal end of the elongate shaft, a distal side opening in a sidewall of the elongate shaft.

Figure 10:
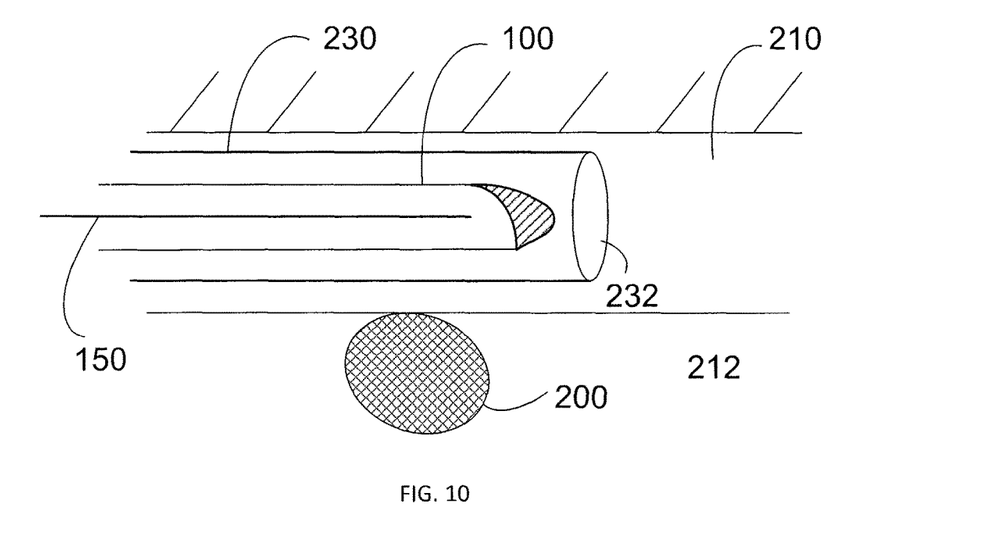
FIG. 10 illustrates an enlarged view of the fourth step in the method of FIG. 9.

FIG. 10 illustrates an enlarged view of the fourth step in the method of FIG. 9. In the zoomed in view, the reentry catheter 100 includes an elongate medical device 150 that is configured to pass through the reentry catheter 100.

Figure 11:
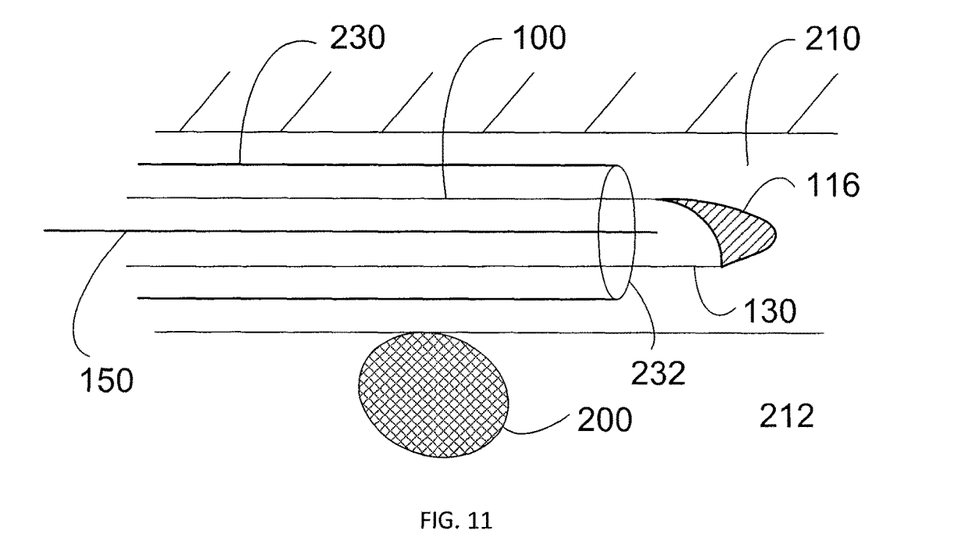
FIG. 11 illustrates an enlarged view of a fifth step in the method of using a reentry catheter.

FIG. 11 illustrates an enlarged view of a fifth step in the method of using a reentry catheter. In this step, the operator advances the reentry catheter 100 until the movable cover 130 is distal to the distal opening 232 of the first catheter 230. The operator may use imaging device to image the distal opening 232, the J-shape filler 116, and the movable cover 130. A distance between the J-shaped filler 116 and the distal opening 232 may be used to identify whether the reentry catheter 100 is in the desired position distal to the distal opening 232. A preferred distance between the J-shaped filler 116 and the distal opening 232 is about 3 mm to about 5 mm.

Figure 12:
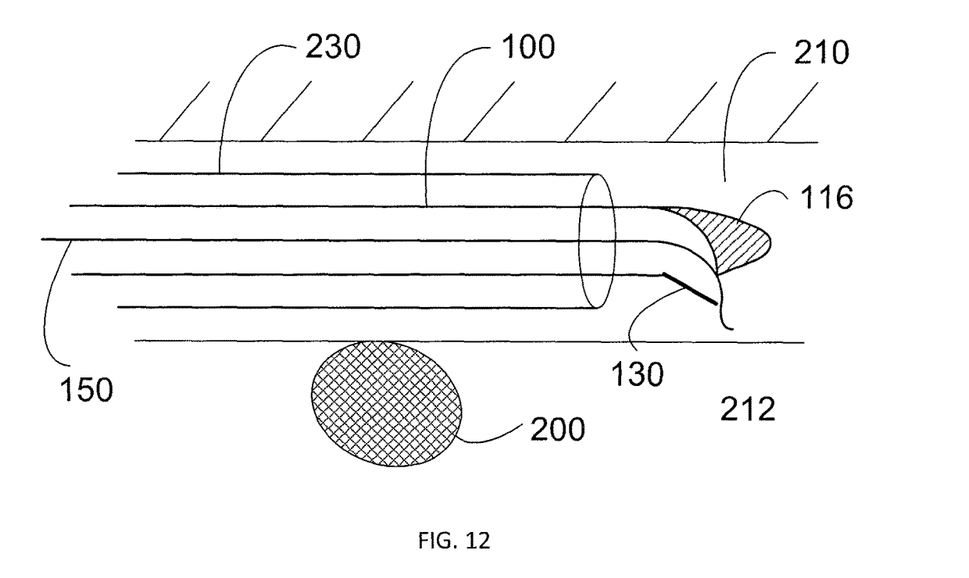
FIG. 12 illustrates an enlarged view of a sixth step in the method of using a reentry catheter.

FIG. 12 illustrates an enlarged view of a sixth step in the method of using a reentry catheter. In this step, the operator feeds the elongate medical device 150 until it pops open the movable cover 130. The moveable cover 130 may be used to puncture back into the true lumen 212.

Figure 13:
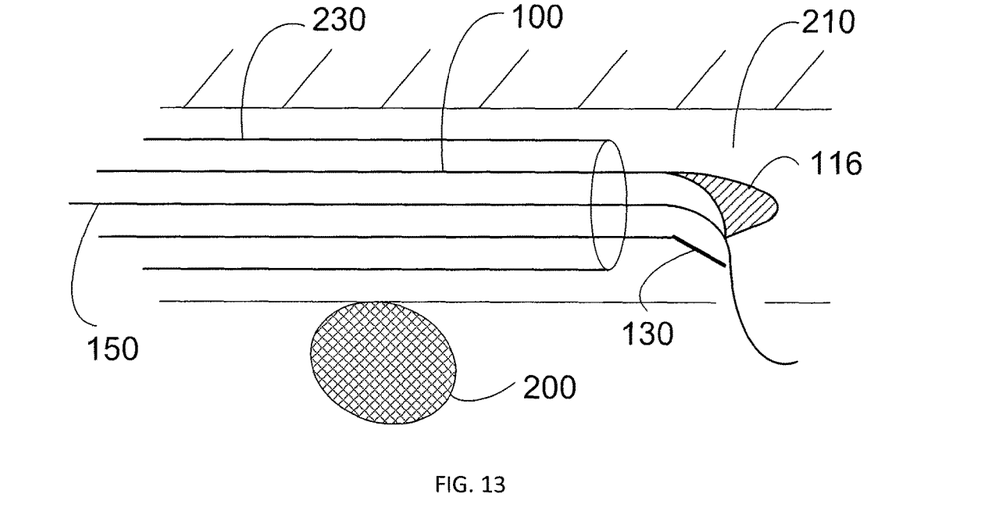
FIG. 13 illustrates an enlarged view of a seventh step in the method of using a reentry catheter.

FIG. 13 illustrates an enlarged view of a seventh step in the method of using a reentry catheter. In this step, the elongate medical device 150 reenters the true lumen 212 by opening the movable cover 130 and puncturing into the true lumen 212.

Figure 14:
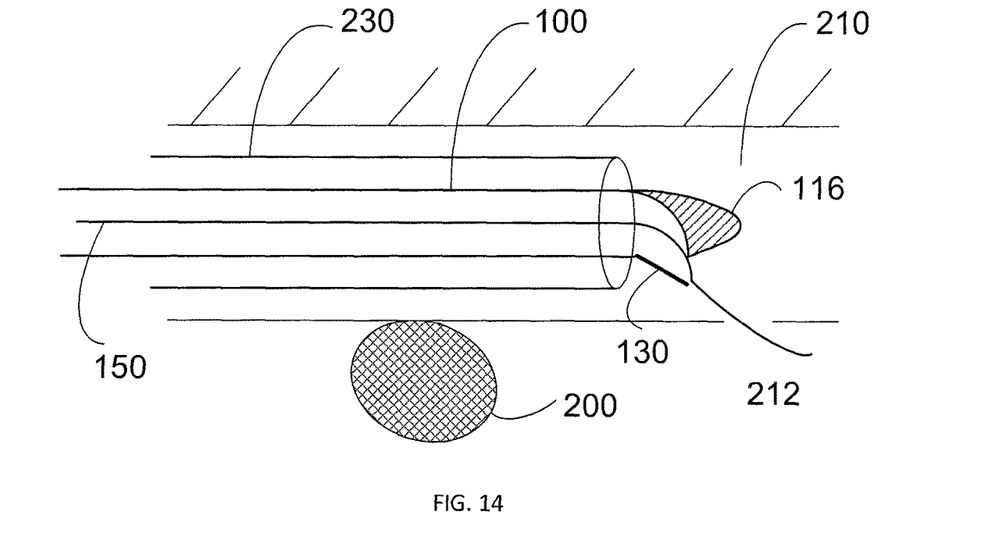
FIG. 14 illustrates an enlarged view of an eighth step in the method of using a reentry catheter.

FIG. 14 illustrates an enlarged view of an eighth step in the method of using a reentry catheter. In this step, the operator started to withdraw the reentry catheter 100 back to the first catheter 230. Because the movable cover 130 is biased to a closed position, the reentry catheter 100 does not cause unnecessary trauma to the vessel wall when moving inside the vessel wall 210.

Figure 15:
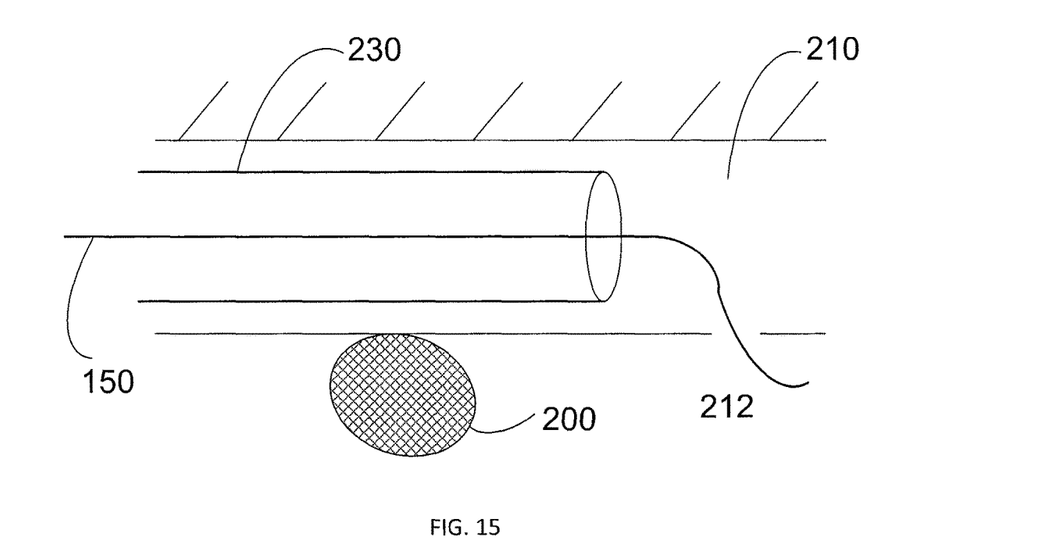
FIG. 15 illustrates an enlarged view of a ninth step in the method of using a reentry catheter.

FIG. 15 illustrates an enlarged view of a ninth step in the method of using a reentry catheter. In this step, the reentry catheter 100 is removed from the first catheter 230.

Figure 16:
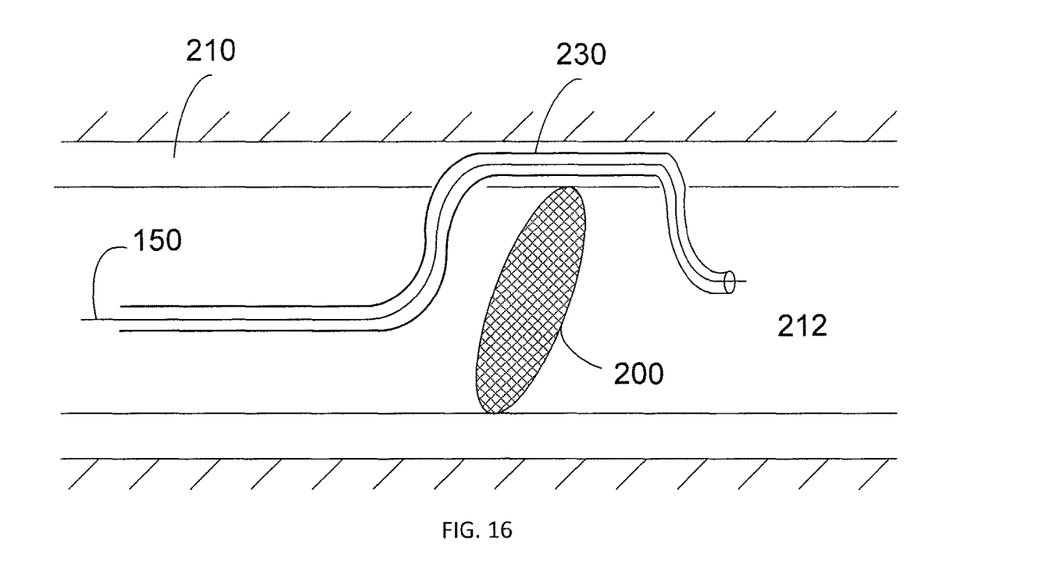
FIG. 16 illustrates a tenth step in the method of using a reentry catheter.

FIG. 16 illustrates a tenth step in the method of using a reentry catheter. In this step, the operator feeds the first catheter 230 over the elongate medical device 150 into the true lumen 212. The first catheter 230 may be a balloon catheter or other catheters used in endovascular treatments.

The disclosed reentry catheter has a movable cover that is biased closed. This prevents bodily matter from entering the reentry catheter after re-entry is achieved. The biasing of the movable cover may be controlled by a spring, magnet, stopper, hinge pins, or shape memory material mechanism. The reentry catheter does not require a needle to puncture through the true lumen which may cause trauma to the vessel. The reentry catheter may instead use the force of the moveable cover to facilitate reentry to eliminate any accidental puncture. Eliminating the needle allow physicians to select almost any type of wire guide they desire to complete the reentry procedure.

While various embodiments of the reentry catheter have been described, it will be apparent to those of ordinary skill in the art that many more embodiments and implementations are possible within the scope of the invention. The different aspects of the described embodiments may be combined together to improve the performance of the reentry catheter. Accordingly, the invention is not to be restricted except in light of the attached claims and their equivalents. Moreover, the advantages described herein are not necessarily the only advantages of the invention and it is not necessarily expected that every embodiment of the invention will achieve all of the advantaged described.

What is claimed is:

1. A method for removing an occlusion in a true lumen, the method comprising:
    inserting a wire guide by puncturing through a vessel wall of the true lumen;
    advancing a first catheter having a distal opening along a wire guide until the distal opening is distal to the occlusion;
    removing the wire guide from the first catheter;
    advancing a reentry catheter inside the first catheter, the reentry catheter having a shaft comprising a proximal opening in a proximal end of the shaft, a J-shaped filler in a distal end of the shaft, a distal side opening in a sidewall of the shaft, the distal side opening adjacent to the J-shaped filler, and a passageway extending between the proximal opening and the distal side opening, the proximal opening, the distal side opening, and the passageway each being configured for the passage of an elongate medical device there through, a movable cover hingedly attached to the sidewall of the shaft, the movable cover biased in a closed position and configured to occlude the distal side opening when in the closed position;
    advancing the reentry catheter until the movable cover is distal to the distal opening of the first catheter; and
    reentering the true lumen by opening the movable cover with the elongate medical device, the movable cover being configured to facilitate reentry to the true lumen in an open position.

2. The method of claim 1, further comprising removing the reentry catheter and leaving the elongate medical device in place.

3. The method of claim 1, wherein the distal side opening is marked by surrounding radiopaque material in the sidewall.

4. The method of claim 1, wherein the movable cover comprises one of the following mechanisms: a spring, a magnet, a stopper, or a hinge pin.

5. The method of claim 1, wherein the movable cover comprises shape memory material.

6. The method of claim 5, wherein the movable cover comprises radiopaque material.

7. The method of claim 5, further comprising feeding the first catheter over the elongate medical device into the true lumen.

8. The method of claim 1, wherein the elongate medical device comprises radiopaque material at a distal end thereof.

9. A method for removing an occlusion in a true lumen, comprising:
    providing an elongate medical device comprising a manipulating device at a proximal end of the elongate medical device;
    providing a shaft comprising a proximal opening in a proximal end of the shaft, a J-shaped filler in a distal end of the shaft, a distal side opening in a sidewall of the shaft, the distal side opening adjacent to the J-shaped filler, and a passageway extending between the proximal opening and the distal side opening;
    passing the elongate medical device through the proximal opening, the distal side opening, and the passageway, wherein a movable cover is hingedly attached to the sidewall of the shaft, the movable cover biased in a closed position and configured to occlude the distal side opening when in the closed position; and
    engaging and popping open, by a distal end of the elongate medical device, the movable cover, the opened movable cover engages a vessel wall of a true lumen and facilitates reentry to the true lumen during a reentry procedure.

10. The method of claim 9, wherein the distal side opening is marked by surrounding radiopaque material in the sidewall.

11. The method of claim 9, wherein the movable cover comprises one of the following mechanisms: a spring, a magnet, a stopper, or a hinge pin.

12. The method of claim 9, wherein the movable cover comprises a sharp edge configured to partially penetrate the vessel wall of the true lumen.

13. The method of claim 9, wherein the movable cover comprises radiopaque material.

14. The method of claim 9, wherein the J-shaped filler comprises radiopaque material.

15. The method of claim 9, wherein the elongate medical device comprises a guide wire including radiopaque material at a distal end thereof.

* * * * *